(12) United States Patent
Ghosh et al.

(10) Patent No.: US 6,667,339 B2
(45) Date of Patent: *Dec. 23, 2003

(54) VANADIUM (IV) COMPLEXES CONTAINING CATECHOLATE LIGAND AND HAVING SPERMICIDAL ACTIVITY

(75) Inventors: Phalguni Ghosh, St. Anthony, MN (US); Faith M. Uckun, White Bear Lake, MN (US); Osmond D'Cruz, Maplewood, MN (US)

(73) Assignee: Parker Hughes Institute, St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/202,663

(22) Filed: Jul. 23, 2002

(65) Prior Publication Data

US 2003/0013698 A1 Jan. 16, 2003

Related U.S. Application Data

(62) Division of application No. 09/957,524, filed on Sep. 19, 2001, now Pat. No. 6,465,450, which is a continuation of application No. PCT/US00/07188, filed on Mar. 17, 2000.
(60) Provisional application No. 60/125,306, filed on Mar. 19, 1999.

(51) Int. Cl.[7] .................. A61K 31/28; A61K 31/4745; C07F 9/00; C07D 471/04; A61P 15/16
(52) U.S. Cl. .................. 514/492; 514/185; 514/186; 514/187; 514/184; 514/188; 514/464; 546/2; 546/6; 546/10; 549/210; 549/212
(58) Field of Search .................. 514/492, 185, 514/186, 187, 184, 188, 464; 546/2, 6, 10; 549/210, 212

(56) References Cited

U.S. PATENT DOCUMENTS

| | | | |
|---|---|---|---|
| 3,361,778 A | | 1/1968 | Pedersen |
| 4,707,362 A | | 11/1987 | Nuwayser |
| 5,069,906 A | | 12/1991 | Cohen et al. |
| 6,051,603 A | | 4/2000 | D'Cruz |
| 6,245,808 B1 | | 6/2001 | Uckun et al. |
| 6,337,348 B1 | * | 1/2002 | Uckun et al. .............. 514/492 |
| 6,465,450 B2 | * | 10/2002 | Ghosh et al. .............. 514/185 |

FOREIGN PATENT DOCUMENTS

| | | |
|---|---|---|
| WO | WO 93 14751 | 8/1993 |
| WO | WO 00 27389 | 5/2000 |
| WO | WO 00 35930 | 6/2000 |
| WO | WO 00 56366 | 9/2000 |

OTHER PUBLICATIONS

Aitken, et al., BioEssays 1994; 16:259–267.
Aitken, et al., Biol Reprod 1989; 40:183–197.
Aitken, et al., J. Reprod. Fertil. 1993; 97:441–450.
Alvarez, et al., J Androl 1987; 8:338–348.
Bourinbaiar, et al., Life Sci 1994; 54:PL 5–9.
Byczkowski, et al., Bull Environ Contam Toxicol 1988; 41:696–703.
D'Cruz et al., *Advances in Reproduction*, vol. 1, No. 2, 1998, pp. 101–123.
D'Cruz et al., *Biology of Reproduction*, vol. 58, 1998, pp. 1515–1526.
D'Cruz et al., *Biology of Reproduction*, vol. 60, 1999, pp. 4435–4444.
D'Cruz et al., *Molecular Human Reproduction*, vol. 4, No. 7, 1998, pp. 683–693.
Evans, D. F. *J. Chem. Soc.* 1959, 2003.
Galeffi et al., *Inorganic Chemistry*, Vol 129, No. 1, 1987, pp. 1–5.
Galeffi et al., *Inorganic Chemistry*, vol. 160, No. 1, 1989, pp. 87–91.
Galeffi et al., *New Journal of Chemistry*, vol. 8, No. 7, 1984, pp. 481–484.
Ghosh, et al., *Abstracts of Papers of the American Chemical Society*, vol. 217, No. 1, 1999, p. 322.
Hawkins et al., *Inorganic Chemistry*, vol. 28, No. 6, 1989, pp. 1084–1087.
International Search Report dated Mar. 5, 2001 for PCT/US00/07188.
Jones, et al., Fertil Steril 1979; 31:531–537.
Kotchevar et al., *J. of Physical Chemistry*, vol. 102, 1992, pp. 10925–10930.
Lal, K. et al., *Bulletin of the Chemical Society of Japan*, vol. 40, No. 5, 1967, pp. 1148–1152.
Lal, Kundan et al., *Chemical Abstracts*, vol. 12, No. 4, 1967, pp. 269–279.
Niruthisard, et al., Sex Transm Dis 1991; 18:176–179.
Sakurai, et al., Biochem Biophys Res Commun 1995; 206:133–137.
Setaka, et al., *J. Catal.* 1969, 15, 209.
Shi, et al., Ann Clin Lab Sci 1996; 26:390–49.
Simpson et al., *Inorganic Chemistry*, Vol 31, No. 21, 1992, pp. 4308–4313.
Wilborn, et al., Fertil Steril 1983; 39:717–719.
Younes, et al., Toxicology 1991; 66:63–74.

* cited by examiner

Primary Examiner—Evelyn Mei Huang
(74) Attorney, Agent, or Firm—Merchant & Gould P.C.

(57) ABSTRACT

Vanadium (IV) complexes containing a substituted or unsubstituted catecholate ligand, and the spermicidal activity of such compounds. Preferred compounds are vanadocene (IV) complexes containing alkyl substituted catecholate ligands.

10 Claims, 6 Drawing Sheets

Cyclic Votammogram of $Cp_2V(cat)$ in $CH_3CN$.

Scan Rate = 200 mV/s; 0.1 M $^nBu_4NPF_6$; Ag/0.1 M $AgNO_3$ reference electrode; Pt disk working electrode. Potential is shown vs. Ferrocene/Ferrocenium in $CH_3CN$.

ORTEP Diagram of Cp₂V(cat)

ORTEP Diagram of $Cp_2V(catCl_4)$

UV-vis spectrum of $Cp_2V$ (Cat) in acetonitrile. $[Cp_2V(Cat)]$=0.22 mM

Temperature = 298 k; Microwave Frequency = 20mW at 9.64 GHz; Modulation Amplitude = 8.280 G at 100[$Cp_2V(Cat)$] = 1x10$^{-3}$ M.

VANADIUM (IV) COMPLEXES CONTAINING CATECHOLATE LIGAND AND HAVING SPERMICIDAL ACTIVITY

This application claims benefit of Provisional application Serial No. 60/125,306, filed Mar. 19, 1999 and is a divisional of U.S. patent application Ser. No. 09/957,524, filed Sep. 19, 2001 now U.S. Pat. No. 6,465,450, which is a continuation of PCT/US00/07188 filed Mar. 17, 2000, which was published by the International Bureau in English on Sep. 28, 2000.

FIELD OF THE INVENTION

This invention relates to compositions containing vanadium (IV). More particularly, the invention relates to vanadium (IV) complexes containing a substituted or un-substituted catecholate ligand and having spermicidal activity.

BACKGROUND OF THE INVENTION

The known spermicidal agents, nonoxynol-9 and gramicidin, exert their effects via a detergent-like ability to damage the sperm plasma membrane, perturb its conformation and destroy its semi-permeable nature thereby impairing the sperm motility and egg fertilizing functions (Wilborn, et al., Fertil Steril 1983; 39:717–719; Bourinbaiar, et al., Life Sci 1994; 54:PL 5–9). Because of their non-specific membrane disruptive properties, such vaginal spermicides have been shown to damage the cervicovaginal epithelium, as well, which may lead to a lower degree of protection from sexually transmitted diseases (Niruthisard, et al., Sex Transm Dis 1991; 18:176–179). A novel vaginal contraceptive preferably does not function with the non-specific membrane toxicity mediated by detergent-type action of the currently available vaginal contraceptives.

Vanadium is a physiologically essential element which can be found in one of five (I to V) oxidation states. Several inorganic salts containing vanadium with oxidation state +4 (IV) have been shown to function as modulators of cellular redox potential and to exert pleiotropic effects in multiple biological systems by catalyzing the generation of reactive oxygen intermediates. See, for example, Shi, et al., Ann Clin Lab Sci 1996; 26:390–49; Byczkowski, et al., Bull Environ Contam Toxicol 1988; 41:696–703; Younes, et al., Toxicology 1991; 66:63–74, and Sakurai, et al., Biochem Biophys Res Commun 1995; 206:133–137. Reactive oxygen intermediates have been reported to affect sperm motility by a combination of peroxidation of membrane lipids and proteins (Aitken, et al., Biol Reprod 1989; 40:183–197; Jones, et al., Fertil Steril 1979; 31:531–537). Peroxidative damage to the sperm plasma membrane is an important pathophysiological mechanism in the onset of male infertility (Aitken, et al., BioEssays 1994; 16:259–267). It has also been shown that superoxide radicals generated by the action of xanthine oxidase exert a direct, suppressive effect on many aspects of sperm function (Aitken, et al., J. Reprod. Fertil. 1993; 97:441–450). Sperm are thought to be particularly susceptible to oxidative stress by virtue of their high content of unsaturated fatty acids and their relative paucity of cytoplasmic enzymes for scavenging the reactive oxygen intermediates that initiate lipid peroxidation (Alvarez, et al., J Androl 1987; 8:338–348).

There is a need for new spermicidal compounds, compositions, and method for contraceptive purposes.

SUMMARY OF THE INVENTION

Vanadium (IV) complexes containing a substituted or un-substituted catecholate ligand have now been found to have potent, concentration-dependent spermicidal activity at micromolar concentrations. Examples of vanadium (IV) complexes containing a substituted or un-substituted catecholate ligand of the invention include complexes having the structure of Formula I, or pharmaceutically acceptable salts thereof.

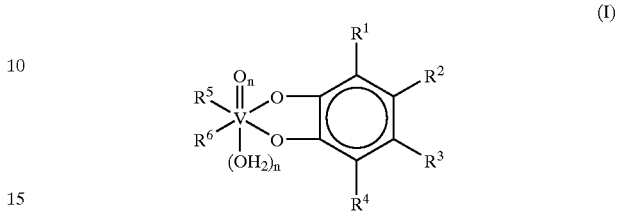

(I)

wherein $R^1$, $R^2$, $R^3$ and $R^4$ are the same or different and are independently selected from H, halo, $OH_2$, $O_3SCF_3$, $N_3$, CN, OCN, SCN, SeCN, $NO_2$, $C_1$–$C_4$ alkyl, $C_1$–$C_4$ alkoxy, and aryl; and n is 0 or 1; and $R^5$ and $R^6$ are the same or different and are either monodentate ligands or $R^5$ and $R^6$ together comprise a bidentate ligand.

Suitable monodentate ligands include, for example, aryl, halo, $H_2O$, $O_3SCF_3$, $N_3$, COOH, CN, OCN, SCN, SeCN, $NO_2$, $C_1$–$C_4$ alkyl, $C_1$–$C_4$ alkoxy. Preferred monodentate ligands comprises one or more unsubstituted or substituted aromatic ring. More preferred monodentate ligands comprise substituted or un-substituted cyclopentadienyl ligands.

Suitable bidentate ligands include, for example, N,N'; N,O; and O,O' bidentate ligands. Examples of suitable N,N' bidentate ligands include diamines and other such known suitable N,N' bidentate ligands. Examples of diamines include bipyridal, derivatives of bipyridal, bridged bipyridal, such as phenanthroline, derivatives of phenanthroline, and other such compounds. Examples of suitable N,O bidentate ligands include amino acids and Schiff base type groups. Examples of suitable O,O' bidentate ligands include dicarboxylate, 2-hydroxyacetophenone, acetylacetone type and catechol type groups. Preferred bidentate ligands comprise one or more aromatic ring. Preferred examples of suitable bidentate ligands comprising aromatic rings include substituted or un-substituted bipyridyl, bridged bipyridyl, and acetophenone ligands. One example of a bridged bipyridyl includes phenanthroline.

In one embodiment the invention provides "bent sandwich" vanadocene monocatecholate complexes having the structure of Formula II, or pharmaceutically acceptable salts thereof.

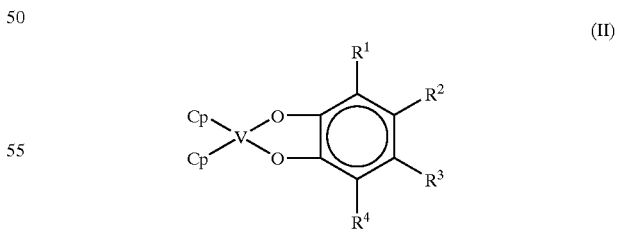

(II)

wherein Cp is unsubstituted cyclopentadienyl, or cyclopentadieneyl substituted with one or more substituents selected from substituted or unsubstituted aryl, $C_1$–$C_4$ alkyl, $C_1$–$C_4$ alkoxy, halo, $OH_2$, $O_3SCF_3$, $N_3$, CN, OCN, SCN, SeCN, $NO_2$. Preferably, Cp is unsubstituted cyclopentadienyl.

$R^1$, $R^2$, $R^3$ and $R^4$ are the same or different and are independently selected from H, halo, $OH_2$, $O_3SCF_3$, $N_3$, CN, OCN, SCN, SeCN, $NO_2$, $C_1$–$C_4$ alkyl, and $C_1$–$C_4$ alkoxy Preferably, electron donating groups, for example electron donating alkyl groups, are present as substituitents of the catecholate ring in positions $R^1$, $R^2$, $R^3$ and/or $R^4$.

Another suitable embodiment of the invention having a bidentate ligand wherein the bidentate ligand is a bipyridyl has the general formula III, shown below, or pharmaceutically acceptable salts thereof:

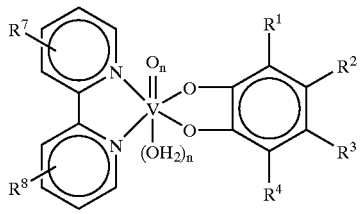

(III)

where $R^7$ and $R^8$ are the same or different and are independently selected from: H, aryl, $C_1$–$C_4$ alkyl, halo, $C_1$–$C_4$ alkoxy, cyano, and nitro; n is 0 or 1; $R^1$, $R^2$, $R^3$ and $R^4$ are the same or different and are independently selected from H, halo, $OH_2$, $O_3SCF_3$, $N_3$, CN, OCN, SCN, SeCN, $NO_2$, $C_1$–$C_4$ alkyl, and $C_1$–$C_4$ alkoxy.

Another suitable embodiment of the invention having a bidentate ligand wherein the bidentate ligand is a bridged bipyridyl has the general formula IV, shown below, or pharmaceutically acceptable salts thereof:

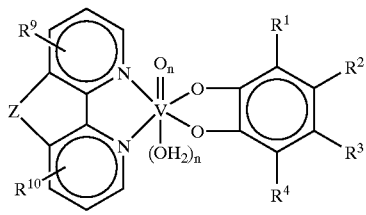

(IV)

where $R^9$ and $R^{10}$ are the same or different and are selected from H, aryl, $C_1$–$C_4$ alkyl, halogen, $C_1$–$C_4$ alkoxy, halogenated alkyl, cyano, and nitro; Z is selected from O, $CH_2$, $CH_2$—$CH_2$, and CH=CH; n is 0 or 1; and halo, $OH_2$, $O_3SCF_3$, $N_3$, CN, OCN, SCN, SeCN, $NO_2$, $C_1$–$C_4$ alkyl, and $C_1$–$C_4$ alkoxy.

Another suitable embodiment of the invention having a bidentate ligand wherein the bidentate ligand is a bridged bipyridyl, and the bridged bipyridyl is phenanthroline, has the general formula V, shown below, or pharmaceutically acceptable salts thereof:

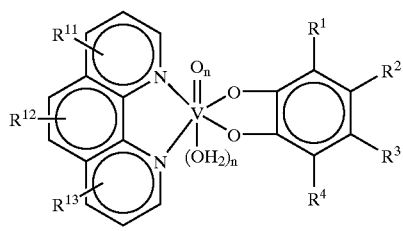

(V)

where $R^{11}$, $R^{12}$ and $R^{13}$ are the same or different and are independently selected from: H, aryl, $C_1$–$C_4$ alkyl, halogen, lower alkoxy, halogenated alkyl, cyano, carboalkoxy (e.g. $C_2$–$C_6$) and nitro; n is 0 or 1; and $R^1$, $R^2$, $R^3$ and $R^4$ are the same or different and are independently selected from H, halo, $OH_2$, $O_3SCF_3$, $N_3$, CN, OCN, SCN, SeCN, $NO_2$, $C_1$–$C_4$ alkyl, and $C_1$–$C_4$ alkoxy.

Another suitable embodiment of the invention having a bidentate ligand wherein the bidentate ligand is an O,O' bidentate ligand, and the complex has the general formula VI, is shown below, or pharmaceutically acceptable salts thereof:

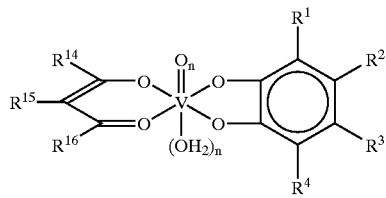

(VI)

where $R^{14}$ and $R^{16}$ are the same or different and are independently selected from: H, aryl, $C_1$–$C_4$ alkyl, and $C_1$–$C_4$ alkoxy, and halogenated alkyl; $R^{15}$ is selected from H, $C_1$–$C_4$ alkyl, halo, $C_1$–$C_4$ alkoxy, and halogenated alkyl; n is 0 or 1; and $R^1$, $R^2$, $R^3$ and $R^4$ are the same or different and are independently selected from H, halo, $OH_2$, $O_3SCF_3$, $N_3$, CN, OCN, SCN, SeCN, $NO_2$, $C_1$–$C_4$ alkyl, and $C_1$–$C_4$ alkoxy.

Accordingly, the present invention includes spermicidal vanadium (IV) complexes containing a substituted or un-substituted catecholate ligand, as well as contraceptive compositions containing a spermicidal effective amount of a vanadium (IV) complexes containing a substituted or un-substituted catecholate ligand and a pharmaceutically acceptable carrier, diluent or vehicle. Another aspect of the present invention is a method of contraception including the step of contacting sperm with a spermicidal effective amount of vanadium (IV) complexes containing a substituted or un-substituted catecholate ligand. Preferably, the vanadium (IV) complexes containing a substituted or un-substituted catecholate ligand is complexed with two cyclopentadienyl ligands.

DETAILED DESCRIPTION

Figure 1:
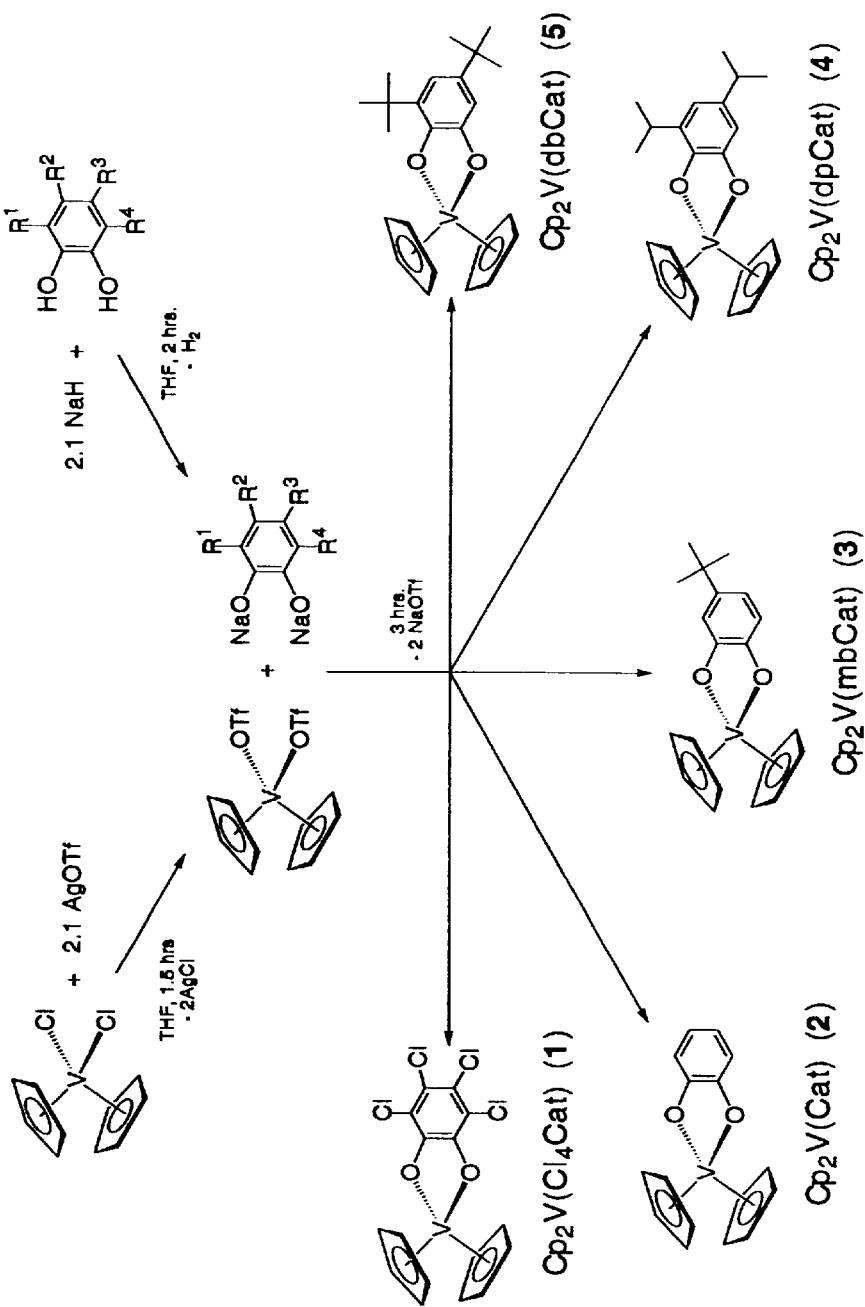
FIG. 1 depicts the reaction scheme used to synthesize vanadocene (IV) chatecholate complexes.

The present invention concerns vanadium (IV) complexes containing a substituted or un-substituted catecholate ligand, and the finding that such vanadium complexes have potent and selective spermicidal activity, and are particularly active and stable spermicidal agents.

Terms and Definitions

As used herein, the following definitions define the stated terms:

"Organometallic compound" is an organic compound comprised of a metal attached directly to carbon (R—M).

"Coordination compound" is a compound formed by the union of a central metal atom or ion with a nonmetal atom, ion or molecule called a ligand or complexing agent.

"Ligand" or a "complexing agent" is a molecule, ion or atom that is attached to the central metal atom or ion of a coordination compound.

"Monodentate ligand" is a ligand having a single donor atom coordinated to the central metal atom or ion.

"Bidentate ligand" is a ligand having two donor atoms coordinated to the same central metal atom or ion.

"Chelate" or "chelated compound" a type of coordination compound in which a central metal ion is attached by chelated ligand containing two or more non-metal atoms in the same molecule. One or more heterocyclic rings are formed with the central metal atom to form the coordination compounds.

"Oxovanadium (IV) complex" is a coordination compound including vanadium as the central metal atom or ion, and the vanadium has an oxidation state of +4 (IV), and is double bonded to oxygen.

"Metallocene" is an organometallic coordination compound containing cyclopentadienyl rings attached to a transition metal or transition metal halide.

"Vanadocene" is a metallocene including vanadium as the transition metal ion.

"Transition metals" is any of a number of elements in which the filling of the outermost shell to eight electrons within a period is interrupted to bring the penultimate shell from 8 to 18 or 32 electrons. Transition metals include elements 21 through 30, 39 through 48, 57 through 80, and from 89 on.

"Halo" is Br, Cl, F, or I.

"Alkyl" is straight chained or branched chained alkyl, and includes halo-substituted alkyl.

"Alkoxy" is straight chained or branched chained alkoxy, and includes an O in the alkyl group.

"Aryl" refers to monovalent unsaturated aromatic carbocyclic radicals having a single ring, such as cyclopentadienyl or phenyl, or multiple condensed rings, such as naphthyl or anthryl, which can be optionally substituted by substituents such as halogen, alkyl, arylalkyl, alkoxy, aralkoxy, and the like.

"Carboalkoxy" is straight chained or branched chained alkoxy, and includes carbamium carbom.

The following is a list of abbreviations and their corresponding meanings which are used throughout the specification:

"Cp" is cyclopentadienyl or cyclopentadiene;

"bpy" is 2,2' bipyridine;

"phen" is phenanthroline;

"acac" is acetyl acetonate;

"cat" is catecholate;

"Otf" is trifluororrmethanesulfonate ($O_3SCF_3$).

Table 1A below provides a glossary of compound number, abbreviated name and compound name of example metallocenes used throughout the specification.

TABLE 1A

Glossary of metallocenes used throughout the specification.

| Compound Number | Abbreviation | Name |
|---|---|---|
| 1 | $Cp_2V$ (catCl$_4$) | Vanadocene tetrachloro catecholate |
| 2 | $Cp_2V$ (cat) | Vanadocene catecholate |
| 3 | $Cp_2V$ (mbcat) | Vanadocene mono-tertbutyl catecholate |
| 4 | $Cp_2V$ (dpcat) | Vanadocene 1,3-diisopropyl catecholate |
| 5 | $Cp_2V$ (dbcat) | Vanadocene 1, 3 ditertbutyl catecholate |

Vanadium

Vanadium is a physiologically essential element that can be found in both anionic and cationic forms with oxidation states ranging from −1 to +5 (I–V). This versatility provides unique properties to vanadium complexes. In particular, the cationic form of vanadium complexes with oxidation state +4 (IV) have been shown to function as modulators of cellular redox potential, regulate enzymatic phosphorylation, and exert pleiotropic effects in multiple biological systems by catalyzing the generation of reactive oxygen species (ROS). Besides the ability of vanadium metal to assume various oxidation states, its coordination chemistry also plays a key role in its interactions with various biomolecules. In particular, organometallic complexes of vanadium (IV) linked to bis(cyclopentadienyl) moieties or vanadocenes exhibit antitumor properties both in vitro and in vivo primarily via oxidative damage.

Human Sperm

Human sperm are known to be exquisitely sensitive to oxidative stress due to the high content of polyunsaturated fatty acids in their cell membranes, the low levels of cytoplasmic enzymes (superoxide dismutase, catalase, and gluthathione peroxidase) for scavenging the reactive oxygen species (ROS) intermediates, that initiate lipid peroxidation, and reduced activity of repair enzymes (exonucleases, endonucleases, glycosidases, and polymerases) to recover from oxidative damage. Reactive oxygen species such as hydrogen peroxide ($H_2O_2$) and hydroxyl radicals ($^\bullet OH$) have been shown to affect sperm motility by a combination of peroxidation of membrane lipids and proteins. Oxidative damage to sperm proteins, carbohydrates, and DNA is an important pathophysiological mechanism in the onset of male infertility. It has also been shown that superoxide radicals generated by the action of xanthine oxidase exert a direct, suppressive effect on sperm function, including loss of motility, impaired capacitation, and sperm-egg interaction.

In our copending patent application, U.S. patent application Ser. No. 09/008,898, which is hereby incorporated herein by reference for all purposes, it is demonstrated in the examples certain bis(cyclopentadienyl)vanadium (IV) complexes have potent spermicidal and apoptosis-inducing properties against human sperm. In fact, very short (<1 minute) exposure to vanadocenes at nanomolar to micromolar concentrations was sufficient to induce complete sperm motility loss, whereas, prolonged exposure of sperm to millimolar concentrations of inorganic vanadium (oxidation state IV and V) salts had no effect on sperm motility. Similarly, in our copending patent application, U.S. patent application Ser. No. 09/187,115, which is hereby incorporated herein by reference for all purposes, certain oxovanadium (IV) compounds at nanomolar to micromolar concentrations was sufficient to induce complete sperm motility loss. Furthermore, none of the other metallocenes (oxidation state IV) containing titanium, zirconium, molybdenum, or hafnium exhibited spermicidal activity.

Since the redox potential and the stability of organovanadium complexes are greatly affected by the complexed ligands, different ligands were selected to test their effects on the spermicidal activity and stability. Vanadocene (IV) complexes containing a substituted or un-substituted catecholato ligand were synthesized. Specific compounds included $Cp_2V(catCl_4)$, $Cp_2V(cat)$, $Cp_2V(mbcat)$, $Cp_2V(dpcat)$, and $Cp_2V(dbcat)$.

These compounds were synthesized and examined for potential spermicidal activity using computer-assisted sperm analysis (CASA). Results presented below provide unprecedented evidence that vanadium complexes containing a substituted catacholato ligand are potent spermicidal agents.

Compounds

Compounds of the invention include vanadium (IV) complexes containing a substituted or un-substituted catecholate ligand. Examples of such compounds include complexes having the structure of Formula I or pharmaceutically acceptable salts thereof.

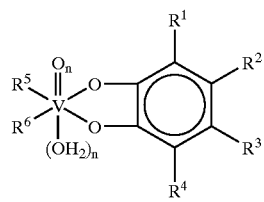

(I)

wherein $R^1$, $R^2$, $R^3$ and $R^4$ are the same or different and are independently selected from H, halo, $OH_2$, $O_3SCF_3$, $N_3$, CN, OCN, SCN, SeCN, $NO_2$, $C_1$–$C_4$ alkyl, $C_1$–$C_4$ alkoxy, and aryl; and n is 0 or 1; and $R^5$ and $R^6$ are the same or different and are either monodentate ligands or $R^5$ and $R^6$ together comprise a bidentate ligand.

Suitable monodentate ligands include, for example, aryl, halo, $H_2O$, $O_3SCF_3$, $N_3$, COOH, CN, OCN, SCN, SeCN, $NO_2$, $C_1$–$C_4$ alkyl, $C_1$–$C_4$ alkoxy. Preferred monodentate ligands comprises one or more unsubstituted or substituted aromatic ring. More preferred monodentate ligands comprise substituted or un-substituted cyclopentadienyl ligands.

Suitable bidentate ligands include, for example, N,N'; N,O; and O,O' bidentate ligands. Examples of suitable N,N' bidentate ligands include diamines and other such known suitable N,N' bidentate ligands. Examples of diamines include bipyridal, derivatives of bipyridal, bridged bipyridal, such as phenanthroline, derivatives of phenanthroline, and other such compounds. Examples of suitable N,O bidentate ligands include amino acids and Schiff base type groups. Examples of suitable O,O' bidentate ligands include dicarboxylate, 2-hydroxyacetophenone, acetylacetone type and catechol type groups. Preferred bidentate ligands comprise one or more aromatic ring. Preferred examples of suitable bidentate ligands comprising aromatic rings include substituted or un-substituted bipyridyl, bridged bipyridyl, and acetophenone ligands. One example of a bridged bipyridyl includes phenanthroline.

Preferred compounds of the invention are those having the formulas II, III, IV, V and VI shown and described below. Most preferred are compounds having formula II shown and described below.

Some preferred compounds include "bent sandwich" vanadocene monocatecholate complexes having the structure of Formula II, or pharmaceutically acceptable salts thereof:

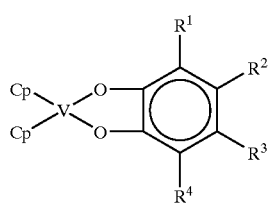

(II)

wherein Cp is unsubstituted cyclopentadienyl, or cyclopentadieneyl substituted with one or more substituents selected from substituted or unsubstituted aryl, $C_1$–$C_4$ alkyl, $C_1$–$C_4$ alkoxy, halo, $OH_2$, $O_3SCF_3$, $N_3$, CN, OCN, SCN, SeCN, $NO_2$. Preferably, Cp is unsubstituted cyclopentadienyl.

$R^1$, $R^2$, $R^3$ and $R^4$ are the same or different and are independently selected from H, halo, $OH_2$, $O_3SCF_3$, $N_3$, CN, OCN, SCN, SeCN, $NO_2$, $C_1$–$C_4$ alkyl, and $C_1$–$C_4$ alkoxy Preferably, electron donating groups, for example electron donating alkyl groups, are present as substituitents of the catecholate ring in positions $R^1$, $R^2$, $R^3$ and/or $R^4$.

Particularly preferred compounds include Cp2 V(cat), Cp2V(mbcat), Cp2V(dpcat), compounds 2–4 shown in FIG. 1.

Another example of compounds of the invention are complexes having a bidentate ligand wherein the bidentate ligand is a bipyridyl has the general formula III, shown below, or pharmaceutically acceptable salts thereof:

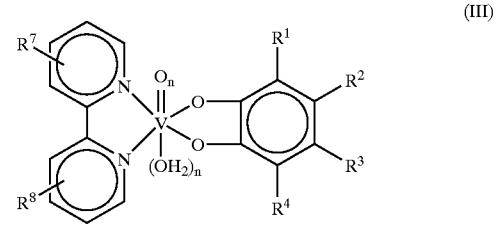

(III)

where $R^7$ and $R^8$ are the same or different and are independently selected from: H. aryl, $C_1$–$C_4$ alkyl, halo, $C_1$–$C_4$ alkoxy, carboalkoxy (e.g. $C_2$–$C_6$), cyano, and nitro; n is 0 or 1; $R^1$, $R^2$, $R^3$ and $R^4$ are the same or different and are independently selected from H, halo, $OH_2$, $O_3SCF_3$, $N_3$, CN, OCN, SCN, SeCN, $NO_2$, $C_1$–$C_4$ alkyl, and $C_1$–$C_4$ alkoxy.

Another example of compounds of the invention include complexes having a bidentate ligand wherein the bidentate ligand is a bridged bipyridyl has the general formula IV, shown below, or pharmaceutically acceptable salts thereof.

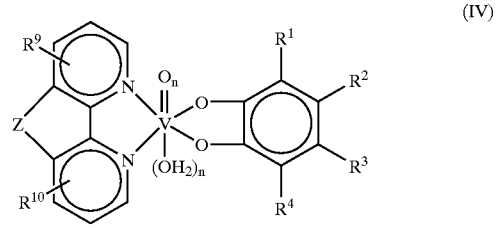

(IV)

where $R^9$ and $R^{10}$ are the same or different and are selected from H, aryl, $C_1$–$C_4$ alkyl, halogen, $C_1$–$C_4$ alkoxy, halogenated alkyl, cyano, carboalkoxy (e.g. $C_2$–$C_6$) and nitro; Z is selected from O, $CH_2$, $CH_2$—$CH_2$, and CH=CH; n is 0 or 1; and halo, $OH_2$, $O_3SCF_3$, $N_3$, CN, OCN, SCN, SeCN, $NO_2$, $C_1$–$C_4$ alkyl, and $C_1$–$C_4$ alkoxy.

Another example of compounds of the invention include complexes having a bidentate ligand wherein the bidentate ligand is a bridged bipyridyl, and the bridged bipyridyl is phenanthroline, has the general formula V, shown below, or pharmaceutically acceptable salts thereof:

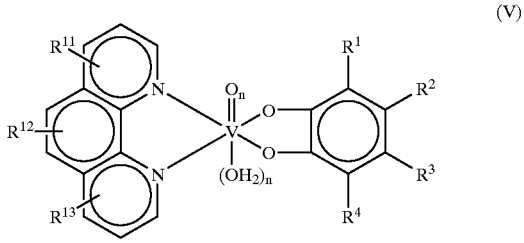

(V)

where $R^{11}$, $R^{12}$ and $R^{13}$ are the same or different and are independently selected from: H, aryl, $C_1$–$C_4$ alkyl, halogen, lower alkoxy, halogenated alkyl, cyano, carboalkoxy (e.g. $C_2$–$C_6$) and nitro; n is 0 or 1; and $R^1$, $R^2$, $R^3$ and $R^4$ are the same or different and are independently selected from H, halo, $OH_2$, $O_3SCF_3$, $N_3$, CN, OCN, SCN, SeCN, $NO_2$, $C_1$–$C_4$ alkyl, and $C_1$–$C_4$ alkoxy.

Another example of compounds includes complexes having a bidentate ligand wherein the bidentate ligand is an O,O' bidentate ligand, and the complex has the general formula VI, is shown below, or pharmaceutically acceptable salts thereof:

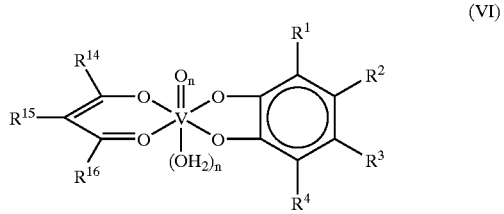

(VI)

where $R^{14}$ and $R^{16}$ are the same or different and are independently selected from: H, aryl, $C_1$–$C_4$ alkyl, and $C_1$–$C_4$ alkoxy, and halogenated alkyl; $R^{15}$ is selected from H, $C_1$–$C_4$ alkyl, halo, $C_1$–$C_4$ alkoxy, and halogenated alkyl; n is 0 or 1; and $R^1$, $R^2$, $R^3$ and $R^4$ are the same or different and are independently selected from H, halo, $OH_2$, $O_3SCF_3$, $N_3$, CN, OCN, SCN, SeCN, $NO_2$, $C_1$–$C_4$ alkyl, and $C_1$–$C_4$ alkoxy.

Sperimicidal Use in Mammals

The spermicidal compositions of the present invention are suitable for use in mammals. As used herein, the term "mammals" means any class of higher vertebrates that nourish their young with milk secreted by mammary glands, e.g., humans, rabbits and monkeys.

The spermicides useful in accordance with the present invention include the above-mentioned vanadium complexes where the vanadium metal has an oxidation state of +4.

Thus, the contraceptive compositions of the present invention contain the above-mentioned vanadium(IV) complexes. The total amount of vanadium(IV) complexes (spermicide) thereof will typically range from about 0.05 to 0.5 weight percent based on the weight of the contraceptive composition. Preferably, the amount of spermicide employed will be that amount necessary to achieve the desired spermicidal results. Appropriate amounts can be determined by those skilled in the art. Preferably, the amount of the spermicide employed, a spermicidal effective amount, will comprise from about 0.0025 to 0.025 weight percent, and more preferably from about 0.05 to 0.5 weight percent, based on the weight of the contraceptive composition.

When used in vivo to selectively kill testicular germ cells or testicular germ cell tumors, the administered dose is that effective to have the desired effect, e.g., sufficient to kill essentially all normal germ cells for chemical castration, or sufficient to reduce or eliminate a testicular cell tumor. The appropriate dose can be extrapolated using known methods and relationships. A useful dose will vary with the desired effect, the mode of administration, and the composition administered. In general, the desired dose will be in the range of 1–25 mg/kg body weight.

The compositions of the invention contain not only the spermicide but necessarily pharmaceutically acceptable carriers, diluents or vehicles, i.e., one that appropriately delivers vanadium complexes to a site for contact with sperm or germ cells and provides spermicidal and/or anti-germ cell activity.

One advantageous component in the pharmaceutical composition for administration of a spermicide is a polymeric delivery component as described in U.S. Pat. No. 5,595,980, which patent is incorporated herein by reference. It has been found that such polymeric delivery component enhances effectiveness of a spermicide and reduces vaginal irritation on administration.

In addition to the polymeric component, the balance of the contraceptive compositions, i.e., typically from about 0.1 to 99.8% and often about 50 to 99.8 weight percent, may optionally comprise one or more cosmetic ingredients. Such cosmetic ingredients are known to those skilled in the art and are often referred to in the art as diluents, solvents and adjuvants. Typically cosmetic ingredients include, for example; water, ethyl alcohol, isopropyl alcohol, glycerin, glycerol propylene glycol, sorbitol and other high molecular weight alcohols. In addition, contraceptive compositions may contain minor amounts, e.g. from about 0.1 to 5% weight based on the weight of the contraceptive compositions, of other additives, such as, for example; stabilizers, surfactants, menthol, eucalyptus oil, other essential oils, fragrances, and the like. Polyoxyethylene 20 sorbitan monolaurate is a preferred stabilizer for use in the compositions. Details concerning the selection and amounts of cosmetic ingredients, other additives, and blending procedures are known to those skilled in the art.

The contraceptive compositions of the present invention may be delivered to the vagina of a mammal by any means known to those skilled in the art. Typical forms for delivery of the compositions include, for example; creams, lotions, gels, foams, sponges, suppositories and films. In addition, the compositions of the present invention may be used as personal care lubricants, such as, for example, condom lubricants, and the like. Such lubricants may comprise commonly known ingredients such as, for example: humectants; e.g., glycerin, sorbitol, mannitol, glycols and glycol ethers; buffers, e.g., glucono-d-lactone; germicides or bactericides; e.g., chlorhexidine gluconate; preservatives, e.g., methylparaben; viscosifiers; e.g., hydroxyethyl cellulose, etc.; other adjuvants; e.g., colors and fragrances; in addition to the compositions of the present invention. Those skilled in the art will recognize that the physical properties, e.g., viscosity, of such delivery forms may vary widely. For example, the viscosity of a gel form of the composition of the present invention, e.g., 150,000 centipoise, may be substantially higher than the viscosity of lotion form of the composition of the present invention, e.g., 100 centipoise. The contraceptive compositions may be located within a condom for example. Further details concerning the materials, ingredients, proportions and procedures of such delivery forms are known to those skilled in the art.

The contraceptive compositions of the present invention are preferably administered to the vagina of the mammal in a dosage which is effective to immobilize sperm present in the vagina and/or to inhibit their penetration in cervical mucus. Typical dosages range between about 0.0001 to 0.001 grams of the composition per kilogram of body weight of the mammal.

Inter-vaginal devices may also be used to aid in the administration of the spermicide as described in U.S. Pat. No. 5,069,906.

In administering the spermicide in the form of the above compositions, the compositions may also be formulated to release the spermicide both rapidly and with a prolonged release of the drug. Such a formulation providing both rapid and prolonged release has been described in U.S. Pat. No. 4,707,362, which patent is also incorporated herein.

In administering the spermicide in vivo, it is understood that multiple delivery methods are available, including injection, both systemic and local. The preferred method of delivery is local, e.g., intratesticular injection. Where appropriate, the composition may be directly injected into a testicular germ cell tumor mass.

The invention may be further clarified by reference to the following Examples, which serve to exemplify some of the preferred embodiments, and not to limit the invention.

EXAMPLES

Example 1

Synthesis and Characterization of Vanadocene Catocholato Complexes

Materials and Methods

The general chemical synthesis scheme used to synthesize the various vanadocene catocholato complexes having the structure of Formula II used in this study is depicted in FIG. 1.

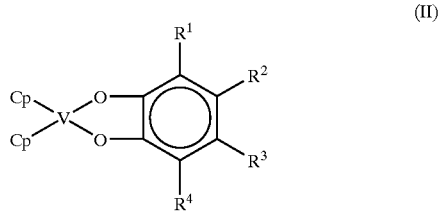

(II)

The compounds in Table 1B were synthesized according to the scheme in FIG. 1.

TABLE 1B

Compounds synthesized according to the scheme presented in FIG. 1.

| Compound | R1 | R2 | R3 | R4 |
|---|---|---|---|---|
| $Cp_2V$ (catCl$_4$) (1) | Cl | Cl | Cl | Cl |
| $Cp_2V$ (cat) (2) | H | H | H | H |
| $Cp_2V$ (mbcat) (3) | H | $^tBu$ | H | H |
| $Cp_2V$ (dpcat) (4) | H | $^tPr$ | H | $^tPr$ |
| $Cp_2V$ (dbcat) (5) | H | $^tBu$ | H | $^tBu$ |

Cp = cyclopentadienyl;
$R^1$, $R^2$, $R^3$, and $R^4$ refer to Formula II;
$^tBu$ = tertiary butyl; and
$^tPr$ = teriary propyl Chemical Synthesis The vanadium (IV) monocatecholate complexes were synthesized according to the scheme presented in FIG. 1; i.e., through the reaction of either $Cp_2VCl_2$ or in situ generated $Cp_2V(OTf)_2$ with disodium salts of various substituted catecholates in tetrahydrofuran slovent. The compounds were purified by chromatography on neutral aluminum oxide, eluting with acetonitrile. An alternate method of synthesis for vanadium (IV) monocatecholate complexes using catechol and excess $N(CH_3)_3$ also works, but the yields are considerably lower; e.g, 7% for $Cp_2V$(cat) and 6% for $Cp_2V$(catCl$_4$).

Infrared Spectra

Infrared spectra were obtained on a FT-Nicollet Protege 460 spectrometer as a KBr pellet or nujol mull. IR spectra are reported in cm$^{-1}$.

UV/Vis Spectra

A UV/vis polarizer attachment was used for the polarization experiments. UV-vis spectra were recorded in a quartz cell or cuvette on a Beckman Model DU 7400 spectrophotometer and the spectral bands were registered in the 200–800 nm range.

$^1$H NMR

H NMR spectra were recorded on a Varian XL-300 spectrometer operating at 300.110 MHz. Chemical shifts were referenced to residual protio solvent peaks in the sample. Magnetic moments were determined using Evan's Method at 20° C. (Evans, D. F. *J. Chem. Soc.* 1959, 2003).

Mass Spectra

Mass spectra were recorded on a HP G2025A MALDI-TOF mass spectrometer using a-cyano-4-hydroxycinnamic acid as the supporting matrix. Spectra were averaged over 50 shots.

EPR

Electron paramagnetic resonance (EPR) spectra were recorded in PBS (0.015 M NaHPO$_4$, 0.10 M NaCl, 0.02 M KCl, pH 7.2) or acetonitrile on a Bruker ESP 300 EPR spectrometer (9.64 GHz). The g values were calibrated with a Varian strong pitch (0.1% in KCl) standard (g value of 2.0028). The samples for the EPR spectral analysis were studied in a Willmad WG-814 standard TE102 aqueous cell cavity (0.3-mm inner path length) to minimize the dielectric loss.

Electrochemical Measurements

Electrochemical measurements were performed on a Bioanalytical Systems B/W 100 b electrochemical analyzer with internal resistance (IR) compensation. The cyclic voltammograms taken in acetonitrile were obtained in a 0.1 M Bu$_4$NPF$_6$ (TABP) electrolyte solution with a 0.1 M Ag/AgNO$_3$ reference electrode, a Platinum Disc working electrode, and a platinum wire auxiliary electrode. Solutions were purged with nitrogen and scanned at 200 mV/s. Aqueous cyclic voltammograms were taken in a standard PBS solution, using a Ag/AgCl reference electrode, a glassy carbon working electrode, and a platinum wire auxiliary electrode. Solutions were purged with nitrogen and scanned at 200 mV/s. All potentials were referenced to the ferrocene-ferrocinium couple ($E_{1/2}$=0.185 V vs Ag/AgCl in PBS).

Elemental Analyses

Elemental analyses were performed by Atlantic Microlab, Inc. (Norcross, Ga.).

Crystallographic Structure Determination of $CP_2V$(catCl$_4$) (1) and $Cp_2V$(cat) (2)

Crystals of $Cp_2V$(catCl$_4$) (1) were grown by vapor diffusion of dichloromethane into pentane of $Cp_2V$(catCl$_4$) (1) at room temperature. A single crystal of dimensions 0.05× 0.04×0.02 mm was attached to a glass fiber using epoxy and was used for cell constant determination and data collection. Crystals of $Cp_2V$(cat) (2) were grown by vapor diffusion of dichloromethane into pentane of $Cp_2V$(cat) (2) at room temperature. A single crystal of dimensions 0.80×0.10×0.02 mm was attached to a glass fiber using epoxy and was used for cell constant determination and data collection.

Data were collected using a Bruker SMART platform CCD (*SMART Software Reference Manual*. Version 5.0, Bruker Analytical X-ray Instruments Inc., Madison, Wis., U.S.A.), with graphite monochromatic MoKa radiation (l=0.71073 Å) at room temperature (293 K.). The SMART software (Bruker, 1998, *SMART Software Reference Manual*. Version 5.0, Bruker Analytical X-ray Instruments Inc., Madison, Wis., U.S.A.) was used for data collection, and the SAINT program (Bruker, 1996, *SAINT Software Reference Manual*. Version 4.0, Bruker Analytical X-ray. Instruments Inc., Madison, Wis., U.S.A.) was used for data reduction. An empirical absorption correction (Bruker, 1997, *SHELXTL—Reference Manual*. Version 5.10, Bruker Analytical X-ray Instruments Inc., Madison, Wis., U.S.A.)

was applied and the structure was solved by direct methods using the SHELXTL V 5.10 suite of programs (Bruker, 1997, *SHELXTL—Reference Manual*. Version 5.10, Bruker Analytical X-ray Instruments Inc., Madison, Wis., U.S.A.). All non-hydrogen atoms were refined anisotropically and the hydrogen atoms were placed in ideal positions and refined as riding atoms with individual isotropic thermal parameters. Atomic scattering factors were taken from the International Tables for X-Ray Crystallography ("*International Tables for X-ray Crystallography*", Volume C, 1991). All calculations were performed on a Pentium computer.

EPR Spin Trapping Experiments

The following is a general procedure for the spin trapping experiments: a $1 \times 10^3$ M solution of the metallocene compound was prepared in water. POBN (5 eq.) was added to the solution, followed by the addition of excess $H_2O_2$ (10 eq.). The solution was transferred to a 50 ml capillary tube, mounted in the cavity of the EPR spectrometer, and the spectrum was taken. The spectra were taken within 90 seconds of the addition of $H_2O_2$ unless otherwise noted, and each spectrum was averaged from four independent scans. The EPR spectra of the POBN-·OH adducts were identified by their doublet of triplet EPR signals of the hydroxyl radical at g=2.008 with hyperfine splitting of the nitrosyl nitrogen, $<A^N>=15 \times 10^{-4}$ cm$^{-1}$, and the β-hydrogen atom, $<A^H>=2.81 \times 10^{-4}$ cm$^{-1}$ using $VOSO_4$ as a standard (Setaka, et al. *J. Catal.* 1969, 15, 209). Control solutions of the organometallic vanadium compounds and POBN indicated no interaction between the compounds and the spin trap. Control solutions of POBN and $H_2O_2$ also indicated no interaction between just the spin trap and $H_2O_2$.

Results

Yield, Stability and Basic Properties

The vanadocene catecholate complexes can be obtained in fairly high yields, ranging from 18 to 39 percent. The magnetic moments of complexes 1–5 were determined to be between $m_{eff}$ 1.60 BM and 1.68 BM. Table 2 shows the percent yields and magnetic moments of the 5 compounds synthesized.

TABLE 2

Synthetic yields and magnetic moments for vanadocene catecholate complexes.

| Compound | Yield % | $\mu_{eff}$ (BM) |
|---|---|---|
| Cp$_2$V (catCl$_4$) (1) | 39 | 1.62 (12) |
| Cp$_2$V (cat) (2) | 26 | 1.63 (12) |
| Cp$_2$V (mbcat) (3) | 21 | 1.66 (12) |
| Cp$_2$V (dpcat) (4) | 31 | 1.68 (12) |
| Cp$_2$V (dbcat) (5) | 18 | 1.60 (12) |

The complexes Cp$_2$V(cat) (2), Cp$_2$V(mbcat) (3), Cp$_2$V(dpcat) (4), and Cp$_2$V(dbcat) (5) have an intense indigo blue color in solution, except for Cp$_2$V(catCl$_4$) (1), which can be purple in acetonitrile. Additionally, complexes 2–5 are soluble in water, while complex Cp$_2$V(catCl$_4$) (1) is not soluble in water.

All of the complexes 1–5 are moderately temperature sensitive, and are maintained at −30° C for prolonged storage without noticeable decomposition. All of the complexes 1–5 are also moderately air sensitive as solids or in solution. The most stable is Cp$_2$V(catCl$_4$) (1) ($t_{1/2}$=about 2 hr. in acetonitrile as determined by cyclic voltammetry and UV-vis spectroscopy), while the least stable is Cp$_2$V(dbcat) (5) ($t_{1/2}$=about 2 min. in acetonitrile). Cp$_2$V(dbcat) (5) is rather unstable even in the absence of oxygen, and is difficult to obtain in high purity.

The vanadocene catecholate complexes 1–5 do not appear to catalize the oxidation of free catechol in solution in the presence of oxygen. However, the free catechol does appear to help stabilize the complexes in solution.

Cyclic Voltammetry

Figure 2:
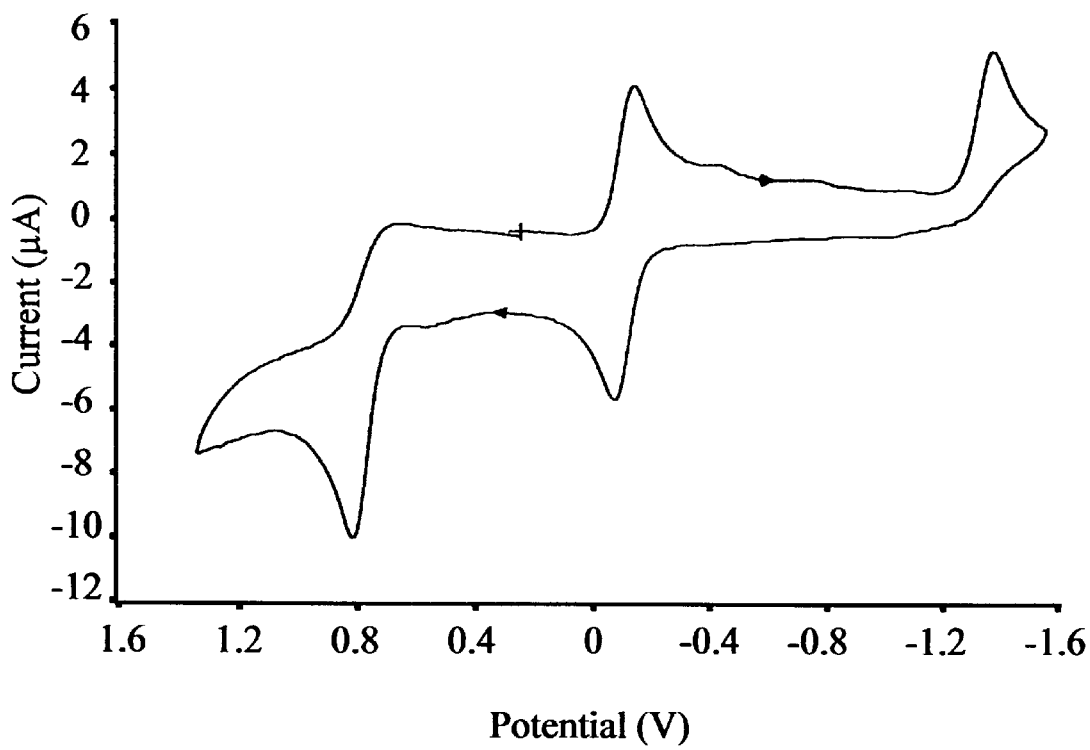
FIG. 2 is a cyclic voltammogram of $Cp_2V(cat)$ in $CH_3CN$.

The vanadoene catecholate complexes 1–4 are easily oxidized. The stabilities of complexes 1–4 follows the oxidization optential for the $V^{IV/V}$ couple with complex Cp$_2$V(catCl$_4$) the most stable and Cp$_2$V(dpcat) (4) the least stable of complexes 1–4. The cyclic voltametry data for compounds 1–4 are shown in Table 3. As can be seen from Table 3, the $V^{IV/V}$ couple can vary depending on the substituents of the catecholate ligand. The cyclic voltagram of Cp$_2$V(cat) (2) in CH$_3$CN is shown in FIG. 2.

TABLE 3

Cyclic voltammetry data for vanadocene catecholate complexes.

| Compound | $E_{1/2}$ (Mv) | $i_c/i_a$ | Solvent |
|---|---|---|---|
| Cp$_2$V (catCl$_4$) (1) | 1096$^a$ | irreversible | Acetonitrile$^c$ |
|  | 282 | 0.97 |  |
|  | −1260$^b$ | irreversible |  |
| Cp$_2$V (cat) (2) | 818$^a$ | irreversible | Acetonitrile$^c$ |
|  | −110 | 0.97 |  |
|  | −1376$^b$ | irreversible |  |
|  | 880$^a$ | irreversible | PBS$^d$ |
|  | 343 | 0.27 |  |
|  | 56 | 0.49 |  |
|  | −840$^b$ | irreversible |  |
| Cp$_2$V (mbcat) (3) | 726 | irreversible | Acetonitrile$^c$ |
|  | −186 | 0.84 |  |
|  | −1374$^b$ | irreversible |  |
| Cp$_2$V (dpcat) (4) | 768 | irreversible | Acetonitrile$^c$ |
|  | −252 | 0.84 |  |
|  | −1408$^b$ | irreversible |  |

$^a$E$_{pa}$;
$^b$E$_{pc}$;
$^c$Potentials given are vs. Cp$_2$Fe$^{+/0}$ in acetonitrile (0.1 M TBAP);
$^d$Potentials are given vs. Ag/AgCl in water (3 M NaCl).

Crystallographic Data

The molecular configurations of for Cp$_2$V(cat) (2) and Cp$_2$V(catCl$_4$) (1) posses a pseudotetrahedral geometry around the central metal ion which is coordinated to two cyclopentadienyl rings and a five-membered catechol chelated ligand. The V—O bond distances are fairly typical compared to other reported vanadium catecholate complexes. The V-Cp centeriod distances are also as expected for a vanadocene complex. Based on the V—O bond distances, it is not likely that the vanadium catecholate complexes are vanadium semi-quinone complexes.

Figure 3:
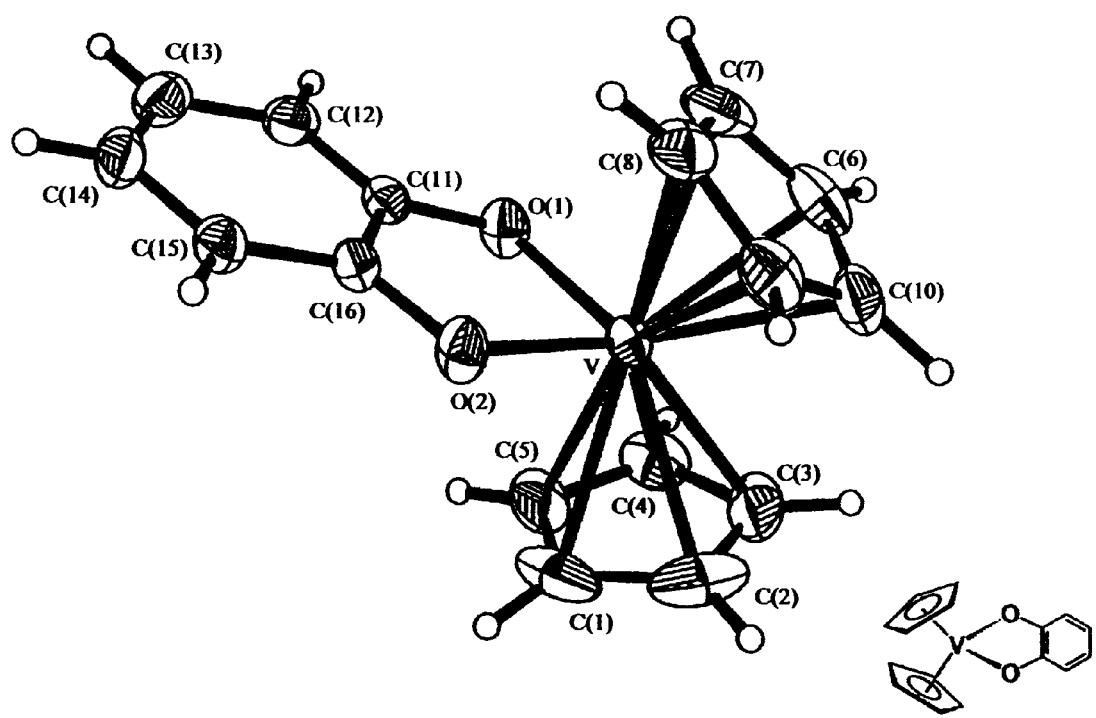
FIG. 3 is an ORTEP diagram of $Cp_2V(cat)$.
Figure 4:
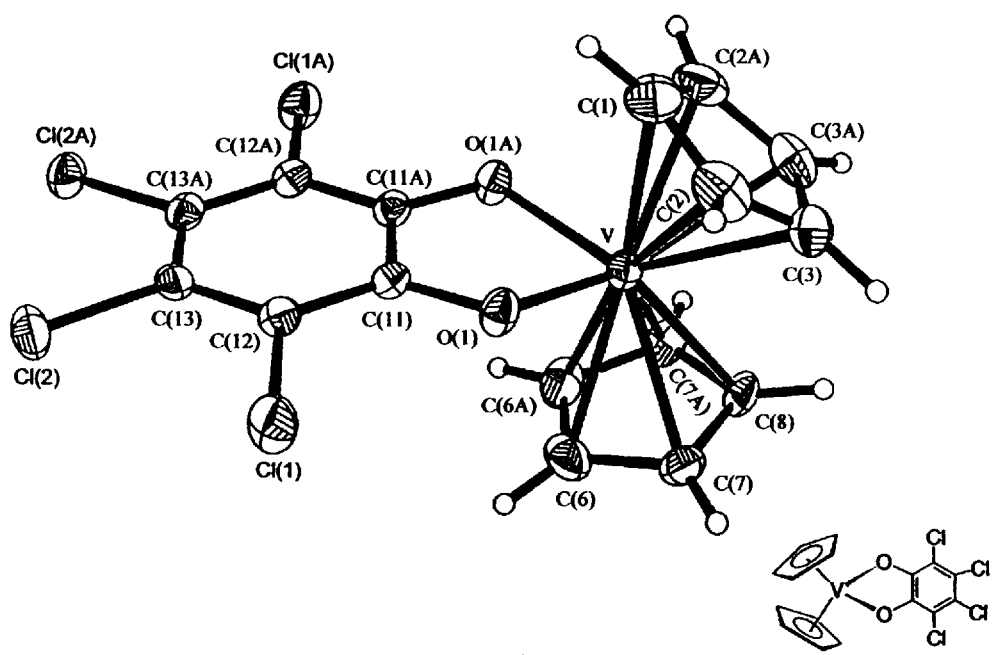
FIG. 4 is an ORTEP diagram of $Cp_2V(catCl_4)$.

Crystallographic data for Cp$_2$V(cat) (2) and Cp$_2$V(catCl$_4$) (1) are summarized in Table 4, selected bond lengths and angles are presented in Table 5, and ORTEP drawings are shown in FIGS. 3 and 4, respectively.

TABLE 4

Crystallographic data for Cp$_2$V (cat) (2) and Cp$_2$V (catCl$_4$) (1).

| Complex | Cp$_2$V (cat) (2) | Cp$_2$V (catCl$_4$) (1) |
|---|---|---|
| Empirical Formula | C$_{16}$H$_{14}$O$_2$V | C$_8$H$_5$Cl$_2$OV$_{0.5}$ |
| Formula weight | 289.21 | 213.49 |
| Crystal system | Monoclinic | Orthorhombic |
| Space group | P2$_1$/n | Pnma |
| Unit cell dimensions | a = 8.5869 (7) A | a = 8.2811 (17) A |
|  | b = 14.5684 (12) A | b = 11.518 (2) A |
|  | c = 11.1829 (9) A | c = 16.333 (3) A |
|  | β = 111.0120 (10)° | β = 90° |
| λ (A) | 0.71073 | 0.71.73 |

TABLE 4-continued

Crystallographic data for Cp$_2$V (cat) (2) and Cp$_2$V (catCl$_4$) (1).

| Complex | Cp$_2$V (cat) (2) | Cp$_2$V (catCl$_4$) (1) |
|---|---|---|
| Volume (A$^3$) | 1305.9 (2) | 1557.8 (5) |
| Z | 4 | 8 |
| Density (g/cm$^3$, Calcd.) | 1.471 | 1.821 |
| Absorption coefficient (mm$^{-1}$) | 0.753 | 1.327 |
| F (000) | 596 | 852 |
| Crystal size (mm) | 0.80 × 0.10 × 0.02 | 0.05 × 0.04 × 0.02 |
| Temperature (K) | 293 (2) | 293 (2) |
| θ range for data collection (°) | 2.40–28.30 | 2.16–28.21 |
| Limiting indices | −10 < h < 10 | −10 < h < 10 |
| | −17 < k < 19 | −15 < k < 12 |
| | −14 < I < 14 | −19 < I < 20 |
| Reflections collected | 7736 | 9131 |
| Independent reflections | 2955 | 1924 |
| Restraints | 0 | 0 |
| Parameters | 173 | 110 |
| Final R, Rw[1 > 2s(1)] | 6.30%, 15.18% | 3.05%, 4.99% |
| Goodness-of-fit on F$^2$ | 1.097 | 0.624 |

TABLE 5

Selected bond angles and distances Cp$_2$V (cat) (2) and Cp$_2$V (catCl$_4$) (1).

| Cp$_2$V (cat) (2) | | Cp$_2$V (catCl$_4$) (1) | |
|---|---|---|---|
| V—O(1) | 1.971(3) A | V—O(1) | 1.995(2) A |
| V—O(2) | 1.975(3) A | V—O(2) | 1.995(2) A |
| V—Cp(A) | 1.99 A | V—Cp(A) | 1.97 A |
| V—Cp(B) | 1.99 A | V—Cp(B) | 1.98 A |
| O1-V—O(2) | 81.125(11)° | O1-V—O(2) | 80.65(9)° |
| Cp(A)—V—Cp(B) | 136.49° | Cp(A)—V—Cp(B) | 134.07° |

UV-Vis Spectral Data

Figure 5:
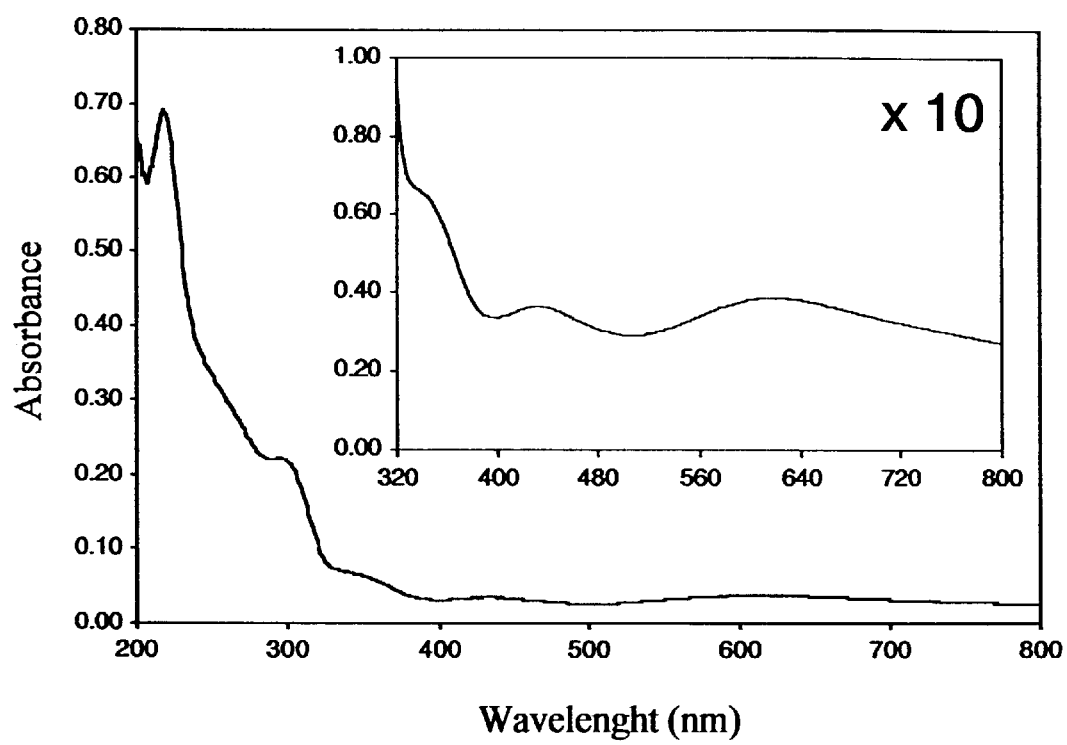
FIG. 5 shows a UV-vis spectrum of $Cp_2V(cat)$ in $CH_3CN$.

UV-vis spectral data for vanadocene catecholate compounds 1–5 in CH$_3$CN are shown in Table 6, and the UV-vis spectrum of Cp$_2$(cat) (2) is shown in FIG. 5. The visible spectra of the vanadocene catecholate complexes are dominated by three moderately intense absorption bands. The first two low energy bands are assigned as catecholate-to V$^{IV}$ charge transfer (LCMT) transitions. These two lower energy bands are observed to shift to higher energy as the substituents on the catecholate ligand are varied from electron withdrawing to electron donating. The third energy transitions, ranging from 315–366 nm for complexes 1–5, are typical for Cp ring to V$^{IV}$ metal charge transfer transitions. Due to overlap this band occasionally appears as a shoulder.

TABLE 6

UV-vis Spectral data for vanadocene catecholate compounds in CH$_3$CN.

| Compound | ε (nm) |
|---|---|
| Cp$_2$V (catCl$_4$) (1) | 555 (1610), 421 (1725), 313 (6344), 232 (39632), 296 (sh), 244 (Sh), 221 (21,000) |
| Cp$_2$V (cat) (2) | 617 (1728), 432 (1603), 337 (3173), 295 (sh), 258 (sh), 217 (37645) |
| Cp$_2$V (mbcat) (3) | 625 (1449), 437 (1249), 335 (2602), 298 (8408), 274 (12643), 255 (16830), 220 (26462) |
| Cp$_2$V (dpcat) (4) | 635 (1500), 436 (1300), 335 (sh), 298 (8408), 296 (sh), 244 (sh), 212 (21,000) |
| Cp$_2$V (dbcat) (5) | 760 (2320), 509 (1960), 366 (2133), 272 (7283), 251 (8628) |

EPR Data

Figure 6:
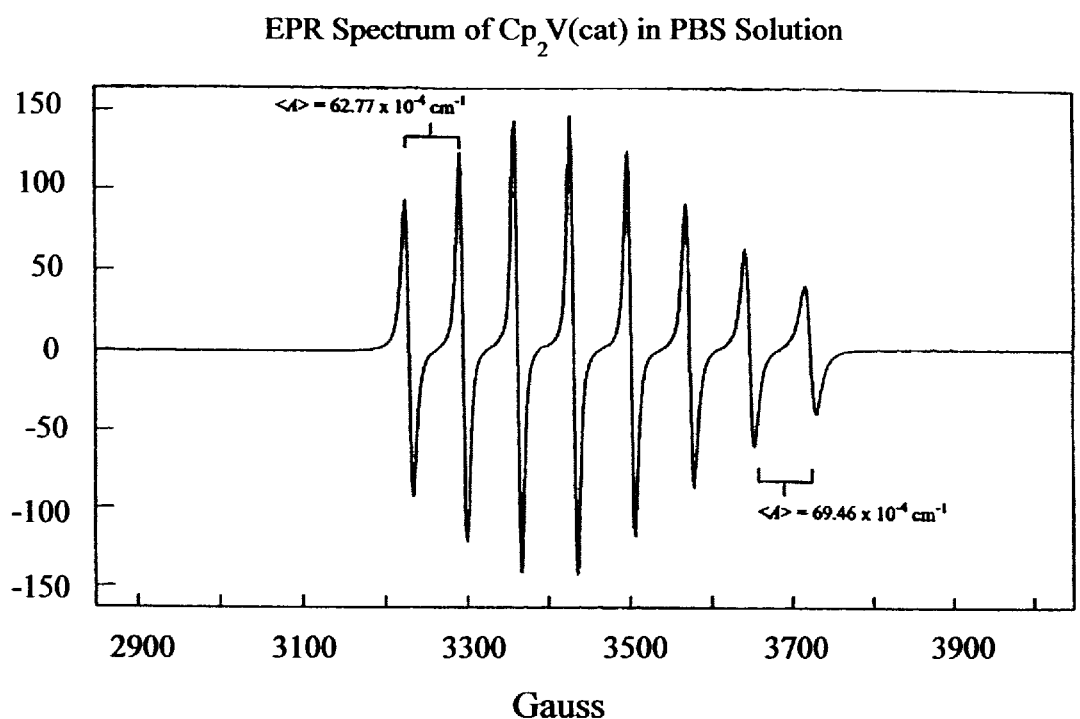
FIG. 6 shows an EPR spectrum of $Cp_2V(cat)$ in PBS solution.

EPR spectral data for vanadocene catecholate compounds 1–5 are shown in Table 7, and the EPR spectrum of Cp2(cat) (2) in PBS is shown in FIG. 6. All complexes 1–5 show an isotropic eight-line resonance as expected from the coupling of the d$^1$ electron spin of V$^{IV}$ with the $^{51}$V nucleus (I=7/2) at room temperature. The isotropic hyperfine coupling constant (<A>=about 65×10$^{-4}$ cm$^{-1}$) is considerably higher than the corresponding Cp$_2$V(1,2-benzenedithiolate) complex (<A>=42×10$^{-4}$ cm$^{-1}$) indicating a lesser π-electron delocalization of the d$^1$ electron for the present series of complexes.

TABLE 7

EPR data for the vanadocene catecholate complexes

| Compound | g (Gauss) | <A> (cm$^{-1}$) | Solvent |
|---|---|---|---|
| Cp$_2$V (catCl$_4$) (1) | 1.98 | 65.2 × 10$^{-4}$ | Acetonitrile |
| Cp$_2$V (cat) (2) | 1.983 | 65.11 × 10$^{-4}$ | Acetonitrile |
| | 1.982 | 65.23 × 10$^{-4}$ | PBS |
| Cp$_2$V (mbcat) (3) | 1.983 | 64.87 × 10$^{-4}$ | Acetonitrile |
| Cp$_2$V (dpcat) (4) | 1.987 | 64.5 × 10$^{-4}$ | Acetonitrile |
| Cp$_2$V (dbcat) (5) | 1.993 | 65.43 × 10$^{-4}$ | Acetonitrile |

Example 2

Effect of Vanadocene (IV) Monocatocholate Complexes on Sperm Motility

Materials and Methods

Sperm Immobilization Assay (SIA)

To evaluate the spermicidal effects of complexes 1–4 a highly motile fraction of pooled donor sperm (n=5) was prepared by discontinuous (90–45%) Percoll gradient (Conception Technologies, San Diego, Calif.) centrifugation and the "swim-up" method as described previously (Aitken et al., 1989, Biol. Reprod. 40:183–197). All donor specimens were obtained after informed consent and in compliance with the guidelines of the Hughes Institutional Review Board. Motile sperm (≧10×10$^6$/ml) were suspended in 1 ml of Biggers, Whitten, and Whittingam's medium (BWW) containing 0.3% BSA (fraction V; Sigma Chemical Co., St. Louis, Mo.) in the presence and absence of serial 2-fold dilutions of test substance (250 μM-1.9 μM) in 0.25% dimethyl sulfoxide (DMSO). For each experiment, fresh stock solutions (100 mM) of vanadium compounds were prepared in DMSO. A corresponding volume of DMSO (0.25%) was added to control sperm suspension. After 3 hours of incubation at 37° C., the percentage of motile sperm was evaluated by computer-assisted sperm motion analysis (CASA) as described previously (Aitken et al., 1989, Supra). The percentages of motilities were compared with those of sham-treated control suspensions of motile sperm. The spermicidal activity of test compounds was expressed as the EC$_{50}$ values (the final concentration of the compound in medium that decreases the proportion of motile sperm by 50%).

To test the effect of duration of incubation on sperm immobilization in the presence of vanadium (IV) complexes, a motile fraction of sperm (10$^7$/ml) was incubated at 37° C. in 1 ml of BWW-0.3% BSA in the presence of 200 μM each of the complexes or 0.2% DMSO alone. At timed intervals (every 5 and 10 minutes) aliquots (4 μl) were transferred to two 20 μm Microcell (Conception Technologies) chambers, and sperm motility was assessed by CASA.

Sperm Kinematic Parameters

For CASA, 4 μl each of sperm suspension was loaded into two 20 μm Microcell chambers placed onto a counting chamber at 37° C. At least 5–8 fields per chamber were scanned for analysis using a Hamilton Thorne Integrated Visual Optical System (IVOS) version 10 instrument (Hamilton Thorne Research Inc., Danvers, Mass.). Each field was recorded for 30 seconds. The Hamilton Thorne computer calibrations were set at 30 frames at a frame rate of 30 images/seconds. Other settings were as follows: minimum contrast 8; minimum size 6; low-size gate, 1.0; high-size gate, 2.9; low-intensity gate, 0.6; high-intensity gate, 1.4; phase-contrast illumination; low path velocity at 10 $\mu$m/seconds and threshold straightness at 80%; magnification factor, 1.95. The performance of the analyzer was periodically checked using the playback function.

The attributes of sperm kinematic parameters evaluated included numbers of motile (MOT) and progressively (PRG) motile sperm; curvilinear velocity (VCL; a measure of the total distance traveled by a given sperm during the acquisition divided by the time elapsed); average path velocity (VAP; the spatially averaged path that eliminates the wobble of the sperm head), straight-line velocity (VSL; the straight-line distance from beginning to end of track divided by time taken), beat-cross frequency (BCF; frequency of lateral head displacement), (ALH; the mean width of sperm head oscillation), and the derivatives, straightness (STR=VSL divided by VAP×100), linearity (LIN=VSL divided by VCL×100, departure of sperm track from a straight line). Data from each individual cell track were recorded and analyzed. At least 200 sperm were analyzed for each aliquot sampled.

A non-linear regression analysis was used to find the $EC_{50}$ and $T_{1/2}$ values (the concentration of the compound, and the time required for 50% sperm motility loss, respectively) from the concentration effect curves.

Results

The spermicidal activities for compounds 1–4 are presented in Table 8. $Cp_2V$(dbcat) (5) was too unstable for testing. $Cp_2V$(dpcat) (4) and $CP_2V$(mbcat) (3) have excellent spermacidal activity ($EC_{50}$=about 0.2 mM). $Cp_2V$(cat) (2) also behaved well as a spermicide ($EC_{50}$=2.4 mM). By comparison, nonoxyl-9, a commercially used spermicide, has an $EC_{50}$=81 mM. the most stable complex $Cp_2V$(catCl$_4$) (1) exhibited no spermacidal activity in the concentration ranges examined.

TABLE 8

Spermacidal activities of the vanadocene catecholate complexes.

| Compound | $EC_{50}$ ($\mu$M)$^a$ | 95% CI | $T_{1/2}$ (min)$^b$ |
|---|---|---|---|
| $Cp_2V$ (catCl$_4$) (1) | >250 | ND | ND |
| $Cp_2V$ (cat) (2) | 2.4 | 1.9–3.5 | 5.8 |
| $Cp_2V$ (mbcat) (3) | 0.1 | 0.06–0.37 | 5.4 |
| $Cp_2V$ (dpcat) (4) | 0.29 | 0.2–0.38 | 0 38 |

$^a$$EC_{50}$ is the concentration of compounds required for 50% sperm motility loss. Motile fractions of human sperm were incubated 3 h with increasing concentrations.
$^b$$T_{1/2}$ is the time required for 50% sperm motility loss. Motile sperm were incubated in the presence of 100 mM of each of the complexes and at timed intervals of 1, 2, or 5 min, sperm motility was assessed by CASA. ND = Not Done.

All publications, patents, and patent documents described herein are incorporated by reference as if fully set forth. The invention described herein may be modified to include alternative embodiments. All such obvious alternatives are within the spirit and scope of the invention, as claimed below.

We claim:

1. A composition comprising:

a) a spermicidal effective amount of a vanadium (IV) complex of Formula I:

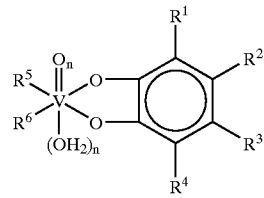

(I)

wherein $R^1$, $R^2$, $R^3$ and $R^4$ are the same or different and are independently selected from H, halo, $OH_2$, $O_3SCF_3$, $N_3$, ON, OCN, SON, SeON, $NO_2$, $C_1$–$C_4$ alkyl, $C_1$–$C_4$ alkoxy and aryl; n is 0 or 1; and $R^5$ and $R^6$ are the same or different and are either an unsubstituted or substituted cyclopentadienyl ligand, with the provisio that
  i) when n=0 and $R^5$ and $R^6$ are monodentate ligands of unsubstituted cyclopentadienyl, $R^1$, $R^2$, $R^3$, and $R^4$ are not each H and are not each Cl b) a pharmaceutically acceptable carrier; and c) a diluent or vehicle.

2. The composition of claim 1, wherein $R^5$ and $R^6$ are each unsubstituted cyclopentadienyl, or substituted cyclopentadieneyl with one or more substituents selected from aryl, $C_1$–$C_4$ alkyl, $C_1$–$C_4$ alkoxy, halo, $OH_2$, $O_3SCF_3$, $N_3$, CN, OCN, SCN, SeCN, $NO_2$.

3. The composition of claim 1, wherein one or more of $R^1$, $R^2$, $R^3$ and $R^4$ are H, halo, or $C_1$–$C_4$ alkyl.

4. The composition of claim 1, wherein the vanadium (IV) complex is selected from the group consisting of $Cp_2V$ (dbcat), $Cp_2V$(mbcat), and $Cp_2V$(dpcat).

5. The composition of claim 4, wherein the vanadium (IV) complex is $Cp_2V$(mbcat) or $Cp_2V$(dpcat).

6. A method for inhibiting the motility of a sperm cell comprising contacting the sperm cell with a spermicidal effective amount of an vanadium (IV) complex of Formula I:

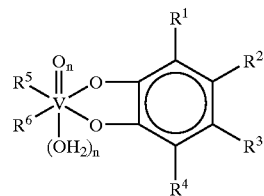

(I)

wherein $R^1$, $R^2$, $R^3$ and $R^4$ are the same or different and are independently selected from H, halo, $OH_2$, $O_3SCF_3$, $N_3$, CN, OCN, SCN, SeCN, $NO_2$, $C_1$–$C_4$ alkyl, $C_1$–$C_4$ alkoxy and aryl; n is 0 or 1; and $R^5$ and $R^6$ are the same or different and are either an unsubstituted or substituted cyclopentadienyl ligand with the provisio that
  i) when n=0 and $R^5$ and $R^6$ are monodentate ligands of unsubstituted cyclopentadienyl, $R^1$, $R^2$, $R^3$, and $R^4$ are not each H and are not each Cl.

7. The method of claim 6, wherein $R^5$ and $R^6$ are each unsubstituted cyclopentadienyl, or substituted cyclopentadienyl with one or more substituents selected from aryl, $C_1$–$C_4$ alkyl, $C_1$–$C_4$ alkoxy, halo, $OH_2$, $O_3SCF_3$, $N_3$, CN, OCN, SCN, SeCN, $NO_2$.

8. The method of claim 7, wherein one or more of $R^1$, $R^2$, $R^3$ and $R^4$ are $C_1$–$C_4$ alkyl.

9. The method of claim 8, wherein the vanadium (IV) complex is selected from the group consisting of $Cp_2V$ (dbcat), $Cp_2V$(mbcat), and $Cp_2V$(dpcat).

10. The method of claim 9, wherein the vanadium (IV) complex is $Cp_2V$(mbcat) or $Cp_2V$(dpcat).

* * * * *

UNITED STATES PATENT AND TRADEMARK OFFICE
CERTIFICATE OF CORRECTION

PATENT NO. : 6,667,339 B2
DATED : December 23, 2003
INVENTOR(S) : Ghosh et al.

It is certified that error appears in the above-identified patent and that said Letters Patent is hereby corrected as shown below:

Title page,
Item [75], Inventors, "Faith M. Uckun," should read -- Fatih M. Uckun, --

Column 3,
Lines 41-42, after "n is 0 or 1; and" insert -- $R^1$, $R^2$, $R^3$ and $R^4$ are the same or different and are independently selected from H, --

Column 5,
Line 38, "carbamium carbom." should read -- carbamium carbon. --

Column 18,
Line 12, "$N_3$, ON, OCN, SON, SeON, $NO_2$, $_{C1-C4}$ alkyl," should read
-- $N_3$, CN, OCN, SCN, SeCn, $NO_2$, $C_1$-$C_4$ alkyl, --
Line 18, "$R^1$, $R^2$, $^{R3}$, and $R^4$" should read -- $R^1$, $R^2$, $R^3$, and $R^4$ --

Signed and Sealed this

Twenty-second Day of June, 2004

JON W. DUDAS
*Acting Director of the United States Patent and Trademark Office*